United States Patent [19]

Hinks

[11] Patent Number: 5,000,182

[45] Date of Patent: Mar. 19, 1991

[54] CARDIAC SYNCHRONIZATION MAGNETIC RESONANCE IMAGING

[75] Inventor: Richard S. Hinks, Cleveland Heights, Ohio

[73] Assignee: Picker International, Inc., Highland Heights, Ohio

[21] Appl. No.: 392,441

[22] Filed: Aug. 11, 1989

[51] Int. Cl.$^5$ ............................................. A61B 5/055
[52] U.S. Cl. ................................ 128/653 A; 128/696; 128/708
[58] Field of Search ................... 128/696, 653 A, 653, 128/708; 324/306

[56] References Cited

U.S. PATENT DOCUMENTS

| | | | |
|---|---|---|---|
| 4,694,837 | 9/1987 | Blakeley et al. ..................... | 128/653 |
| 4,719,424 | 1/1988 | Jimbo et al. .......................... | 324/313 |
| 4,727,882 | 3/1988 | Schneider et al. ................... | 128/653 |
| 4,728,890 | 3/1988 | Pattany et al. ....................... | 324/309 |
| 4,777,957 | 10/1988 | Wehrli et al. ........................ | 128/696 |
| 4,865,043 | 9/1989 | Shimoni ............................... | 128/653 |
| 4,887,609 | 12/1989 | Cole, Jr. ............................... | 128/696 |
| 4,895,157 | 1/1990 | Nambu ................................. | 128/696 |

OTHER PUBLICATIONS

Purge et al., "Respiratory Gating in Magnetic Resonance Imaging at 0.5 Tesla", Radiology, 1984; 151: 521–523.

"Spatial Presaturation: A Method for Suppressing Flow Artifacts and Improving Depiction of Vascular Anatomy in MR Imaging", by Felmlee, et al., Radiology, 164, pp. 559–564, 1987.

"MR Angiography by Selective Inversion Recovery", by Nishimura, et al., Mag. Res. in Med., 4, pp. 193–202, 1987.

"MR Imaging: Clinical Use of the Inversion Recovery Sequence", by Bydder, et al., J. of Computer Assisted Tomography, 9(4): pp. 659–675, Jul./Aug., 1985.

Primary Examiner—Lee S. Cohen
Assistant Examiner—John D. Zele
Attorney, Agent, or Firm—Fay, Sharpe, Beall, Fagan, Minnich & McKee

[57] ABSTRACT

A cardiac monitor (62, 64) monitors the cardiac cycles of a patient in an examination region (10). Each cardiac cycle includes an R-wave (40) at the beginning of the end-diastole. A conditioning pulse trigger (74) enables a preconditioning pulse control (34) to generate a conditioning pulse (42) at a time selected in accordance with the R-wave ($40_{n-1}$) of one cardiac cycle. More specifically, an R-wave predictor (72) predicts when the next R-wave ($40_n$) will occur and the conditioning pulse trigger enables the application of the conditioning pulse ($42_n$) a selected duration before the next predicted R-wave ($40_n$). An imaging sequence trigger (78) enables an image sequence controller (24) to start an imaging sequence in an imaging window ($44_n$) in conjunction with the R-wave ($40_n$). Preferably, the imaging sequence starts immediately with the R-wave ($40_n$) such that the end-diastole stage of the heart is imaged. In this manner, a conditioning pulse, such as an inversion pulse or a saturation pulse, is applied in one cardiac cycle to affect the imaging sequence in the next cardiac cycle. The application of the preconditioning pulse is timed such that the longitudinal magnetization of the blood (54) is near zero (56) during the imaging sequence while the transverse magnetization of cardiac tissue (52) has substantially recovered by the imaging sequence.

15 Claims, 3 Drawing Sheets

CARDIAC SYNCHRONIZATION MAGNETIC RESONANCE IMAGING

BACKGROUND OF THE INVENTION

The present invention relates to the art of magnetic resonance imaging of periodically moving tissue. It finds particular application in conjunction with imaging the heart during and immediately following the end-diastole R-wave of the cardiac cycle. However, it is to be appreciated that the present invention also finds application in conjunction with imaging different portions of the cardiac cycle, other tissue which moves in synchronization with the heart, other periodically moving organs or tissues, and the like.

Conventionally, heart images are $T_1$ weighted spin echo images in which blood is represented in dark and myocardium for defining anatomy is represented in light. The intensity of the signal from blood is a function of two primary factors: (1) flow related spin dephasing and (2) $T_1$ spin relaxation. The flow of the blood causes spin dephasing and signal loss due to motion through a magnetic field gradient. The magnitude of the blood signal is also related to the $T_1$ relaxation time and the sequence of repeat time. Artifacts from blood regions of slow flow are a major cause of degradation in cardiac magnetic resonance images.

Presaturation techniques are most commonly used for suppressing blood signals in order to achieve dark blood/bright myocardium images. Presaturation techniques typically include the application of a frequency selective saturation RF pulse of about 90° in the presence of a magnetic field gradient. This converts the longitudinal magnetization in the selected region into transverse magnetization. The selective 90° RF pulse is typically followed by the application of a gradient "spoiler" pulse which serves to dephase the spins in the saturated region such that they contribute no signal to subsequent imaging sequences.

More specifically, blood and other flowing material, e.g. cerebro spinal fluid, in regions or slices outside of the desired imaging region or slice(s) are presaturated with the above described selective 90° RF pulse. A time delay is interposed between the saturation pulse and the imaging sequence which is gauged to allow the saturated spins from outside of the imaging region to flow into the imaging region. The optimal length of this delay is governed by the rate of flow, the vessel geometry, the distance of the presaturation region from the imaging region, and the longitudinal or $T_1$ relaxation time of the flowing material, and the like.

Although presaturation techniques have been found useful in cardiac imaging, they do have drawbacks. First, a substantial time delay is required between saturation and imaging for effectively eliminating the blood signal from the imaging region. Usually, the presaturation pulse is applied when the R-wave of the patient's cardiac cycle is detected. A delay time long enough to accommodate substantial blood flow into the imaging region is interposed between the presaturation pulse and the start of the image sequences. This blood inflow delay causes a dead time after the R-wave during which image data cannot be acquired. This forecloses the collection of end diastole images and other images during portions of the cardiac cycle immediately following the R-wave. The duration of the inflow delay in human patients is such that the first slice of data is acquired during systole.

Another drawback of saturation methods is the required inclusion of the spoiler gradients. The spoiler gradients are necessary to dephase the signal sufficiently that it does not rephase later during the imaging sequence and contribute to the MR signal during data acquisition. The extra spoiler gradient pulses increase the gradient power requirements of the magnetic resonance system.

Presaturation cardiac images also tend to be degraded by regrowth of the longitudinal magnetization during the inflow accommodating delay time. As the blood inflow delay time is increased, $T_1$ relaxation results in a regrowth of the longitudinal magnetization and a decrease in the effectiveness of the presaturation. For example, the longitudinal magnetization of blood with a $T_1$ relaxation time of 500 msec returns to 20% of its equilibrium value about 110 msec after application of the saturation pulse. This leaves a relatively narrow window between the blood inflow delay and 110 msec after the saturation pulse for imaging the heart.

In inversion recovery imaging, a 180° pulse is applied to invert the spin system which is followed after a delay or inversion time by the selected imaging sequence. The delay or inversion time is selected such that some longitudinal or $T_1$ relaxation occurs before the read out section in which the selected imaging sequence is performed, typically a spin echo or field echo sequence. The signal intensity in the resulting image is a function of primarily the longitudinal or $T_1$ relaxation time and the inversion time (TI). As the inversion time increases from zero toward the longitudinal relaxation time $T_1$, the resulting signal starts at a negative maximum and approaches 0. When the delay time reaches 69% (ln 0.5) of the $T_1$ longitudinal relaxation time, the resulting signal passes through 0. With longer delay times, the signal approaches a positive maximum logrithmically. Stated in absolute value of the magnitude terms, the magnitude of the resultant signal starts at the maximum, decays to zero, and then regrows back toward the maximum. The magnitude of the maximum is affected by the repeat time TR between repetitions of the sequence.

Inversion recovery sequences are commonly used for fat suppression to null signals from fat while collecting image data from other body tissues. The delay time between the inversion pulse and data collection is selected to be near the longitudinal relaxation time for the suppressed fat tissue. In this manner, the signal intensity from the fat is low while the signal from the desired tissue is significantly above the minimum amplitude such that it contributes strongly to the image.

Although inversion recovery techniques have been used in magnetic resonance angiography to differentiate blood from other tissue, they have not heretofore found application in cardiac imaging. For blood with a $T_1$ relaxation time of 500 msec, the longitudinal magnetization is below 20%, between 255–450 msec after the inversion pulse. If an inversion pulse were triggered by the R-wave, the imaging or read out window would be relatively late in the cardiac cycle.

SUMMARY OF THE INVENTION

In accordance with the present invention, a method of magnetic resonance imaging of a cyclically pulsating organ such as the heart is provided. A first preconditioning pulse, e.g. an inversion or presaturation pulse, is applied a selected duration after a preselected point of each cycle. An imaging sequence is conducted during the selected duration before the preconditioning pulse in a cardiac cycle. In this manner, each imaging sequence is affected by the preconditioning pulse applied during the preceding cardiac cycle.

In accordance with a more limited aspect of the present invention, the R-wave of the next cardiac cycle is projected based on the R-wave of preceding cardiac cycles. The preconditioning pulse is applied a selected duration before the projected R-wave such that longitudinal magnetization of nuclei to be imaged is rotated. An imaging sequence is conducted in coordination with the R-wave of the next cardiac cycle.

In accordance with a more limited aspect of the present invention, the imaging sequence is triggered by the second cardiac cycle R-wave.

In accordance with another aspect of the present invention, a magnetic resonance imaging apparatus is provided which includes means for performing the above referenced functions.

One advantage of the present invention is that it enables any part of the cardiac cycle to be imaged, including the end diastole and other portions during and immediately after the R-wave.

Another advantage of the present invention is that it improves cardiac imaging efficiency.

Another advantage of the present invention resides in improved cardiac image quality.

Still further advantages of the present invention will become apparent to those of ordinary skill in the art upon reading and understanding the following detailed description of the preferred embodiments.

BRIEF DESCRIPTION OF THE DRAWINGS

The invention may take form in various steps and arrangements of steps and in various components and arrangements of components. The drawings are only for purposes of illustrating a preferred embodiment and are not to be construed as limiting the invention.

FIG. 3 is an exemplary imaging sequence 44 of FIG. 2C.

DETAILED DESCRIPTION OF THE PREFERRED EMBODIMENTS

Figure 1A:
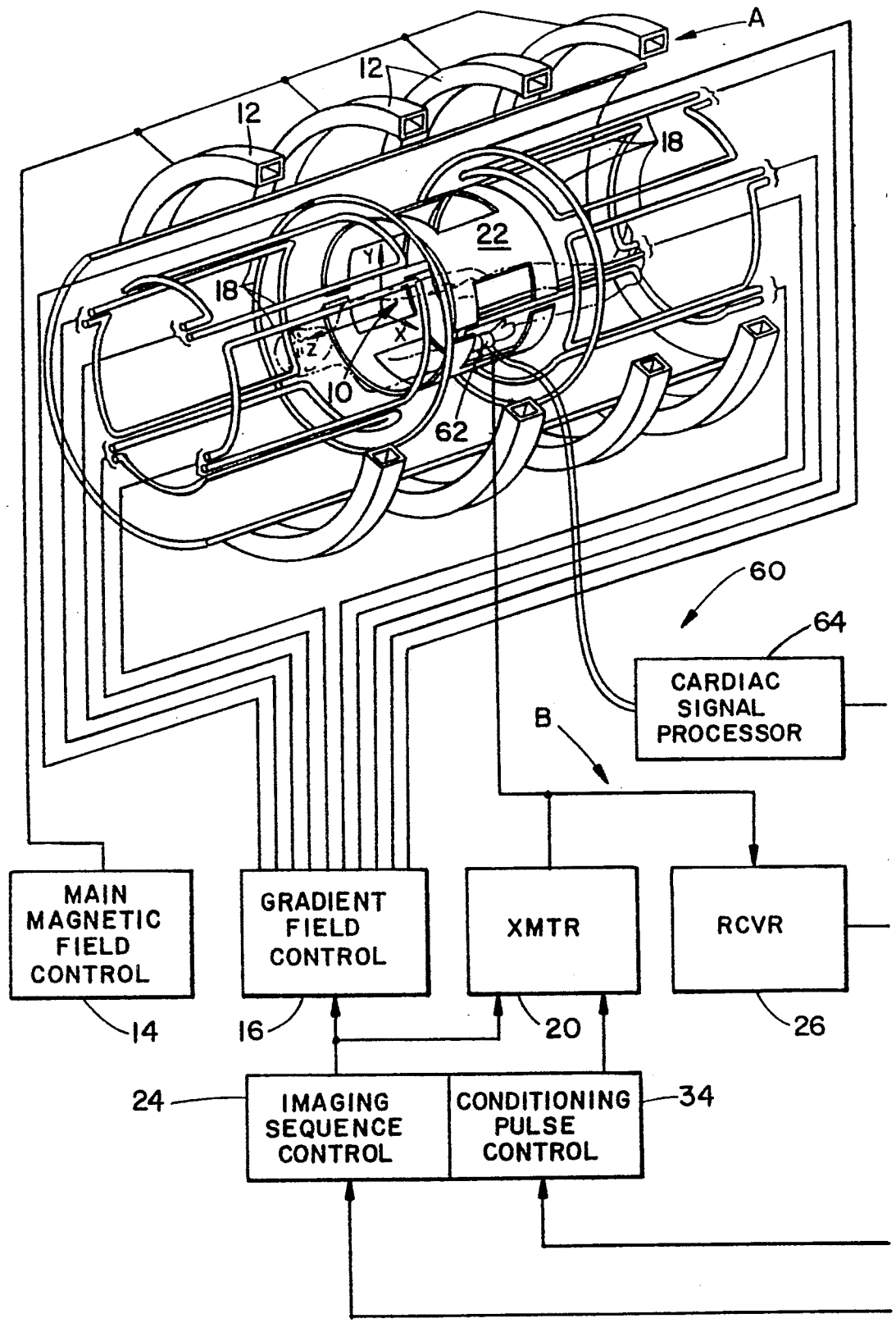
FIG. 1 is a diagrammatic illustration of a magnetic resonance imaging apparatus in accordance with the present invention.

A magnetic resonance imaging system includes a magnetic field means A for generating a static magnetic field through an image region 10 and for selectively causing magnetic field gradients thereacross. The magnetic field means includes a plurality of superconducting, resistance, or permanent magnets 12 which are controlled by a main magnetic field control means 14 to generate a substantially uniform, static magnetic field through the image region. A gradient field control means 16 selectively applies pulses to gradient coils 18 to cause magnetic field gradients at selectable slope and amplitude along three mutually orthogonal axes.

A resonance excitation and recovery means B selectively excites resonance of selected dipoles of the subject in the image region, manipulates the resonance, and collects the generated magnetic resonance signals. The resonance means includes a radio frequency transmitter 20 which selectively applies radio frequency signals to an RF coil 22. These RF pulses are configured to cause 90° rotations of the net magnetization of the selected dipoles, 180° rotations or inversions of the magnetization, and the like as is conventional in the art. An imaging sequence control means 24 controls the radio frequency transmitter 20 and the gradient field control means 16 in order to implement a selected imaging sequence. In a preferred embodiment, the image sequence control means excites and encodes resonance in accordance with the imaging sequence illustrated in U.S. Pat. No. 4,728,890 of Pattany and McNally. The Pattany and McNally sequence is particularly advantageous in that it eliminates blood signal contribution to artifacts attributable to flow related spin dephasing, the other effect which causes a loss of blood signal as discussed above. Optionally, other sequences may be utilized as are known in the art.

Radio frequency magnetic resonance signals emanating from the subject in the image region are picked up by the radio frequency coil 22 or a separate surface coil (not shown) and conveyed to a radio frequency receiver 26. An image reconstruction means preferably includes a two dimensional fast Fourier transform means 28 which transforms magnetic resonance signals received by the receiver into views of an image representation. The views are accumulated in an image memory 30. The image representation may be subject to further processing, stored on tape or disk, displayed on a video monitor 32, or the like.

A flowing tissue or blood and static tissue or myocardium differentiating means conditions the magnetization of the blood and tissue to enable the magnetic resonance signals to be distinguished. In the preferred embodiment, the signal from blood is suppressed relative to the signal from static tissue such that the blood appears black or dark. This enables detail of the myocardium and surrounding tissue to be displayed and differentiated. The blood and static tissue differentiating means includes a conditioning pulse means 34 which causes the transmitter 20 and antenna 22 to apply an inversion pulse, a presaturation pulse, or other radio frequency pulse which has a different effect on the static tissue and blood during the imaging sequence.

Figure 2A:
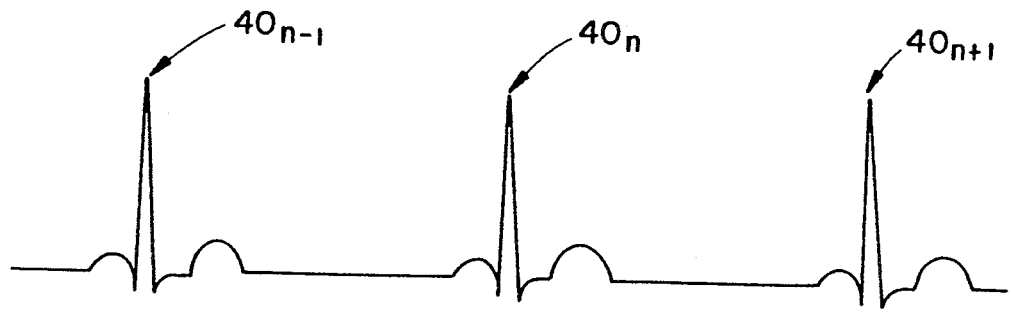
FIGS. 2A, 2B, and 2C are a three part timing diagram illustrating ECG signal, transverse magnetization recovery, and magnetic resonance imaging, respectively.
Figure 2B:
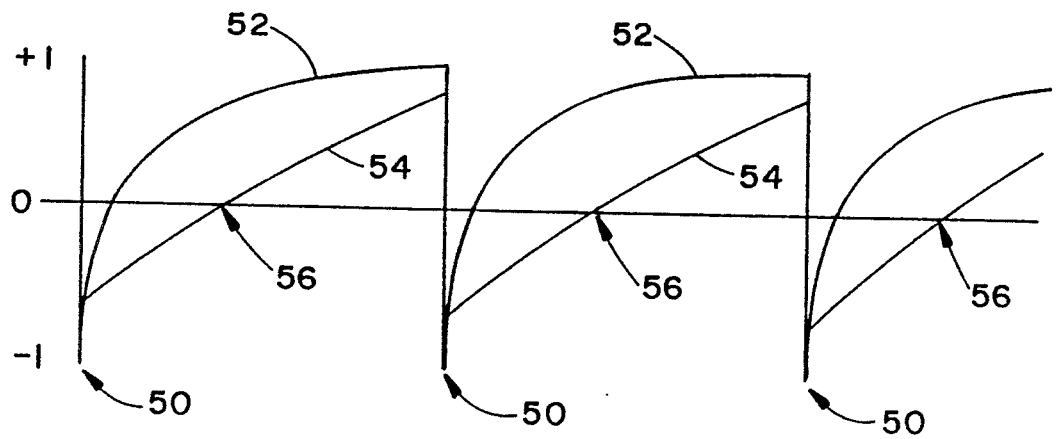
Figure 2C:
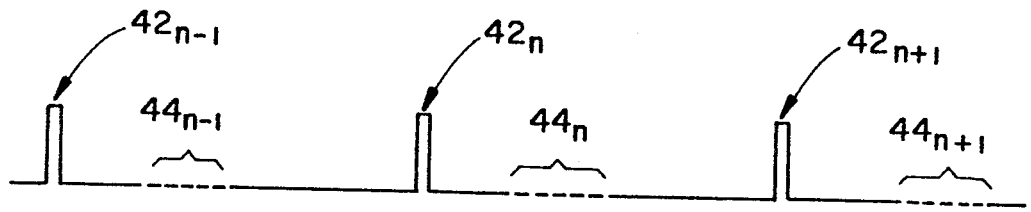

A cardiac timing means C monitors the subject's cardiac cycle and controls the image sequence control 24 and the conditioning pulse mean 34 in accordance therewith. With reference to FIG. 2, the patient's cardiac cycle includes a plurality of R-waves 40 which occur at regular intervals, e.g. every 800–850 msec. In the illustrated embodiment, three of the R-waves are depicted, denoted as R-waves $40_{n-1}$, $40_n$, and $40_{+1}$. In a preferred inversion recovery technique, the conditioning pulse 42 is an inversion pulse that is applied a preselected duration after the preceding R-wave. The RF and gradient pulses of the imaging sequence are applied and magnetic resonance echo data is collected during an imaging window 44. In each cardiac cycle, the imaging sequence is applied after the R-wave followed by the preconditioning pulse corresponding to the next imaging window and cardiac cycle.

The preferred inversion pulse 42 is applied in the absence of any gradients and is non selective, which inverts 50 the magnetization of both the blood and other tissues in the region of interest. The longitudinal magnetization of the static and other non-blood tissue relaxes relatively quickly as illustrated by curve 52. Within about 400 msec, the static materials have relaxed to a level commonly encountered in "$T_1$-weighted" imaging. The longitudinal magnetization of blood relaxes relatively slowly, as illustrated by curve 54. The blood signal decays from its inverted negative maximum at 50, passes through zero crossing at 56, and builds towards a positive maximum. Minimal longitudinal magnetization is present in the blood around the zero crossing. Given a $T_1$ of 500 msec, the absolute value of the longitudinal magnetization is below 20% of its maximum from 255 to 458 msec after the inversion pulse. The imaging window 44 generally spans the zero crossing point 56 and is substantially within this range. Additionally, an image sequence may include motion compensation via gradient moment nulling, such as the sequence illustrated in FIG. 3 and U.S. Pat. No. 4,728,890 to suppress motion and flow artifacts due to spin dephasing.

The inversion pulse $42_n$ is applied a selected duration after R-wave $40_{n-1}$. The imaging sequence in window $44_n$ is commenced a selected time after R-wave $40_n$. If the R-wave $40_n$ is arrhythmic, the imaging sequence may be cancelled or discarded. The inversion pulse application time is selected by projecting the repeat time between R-waves; adding the time between R-wave $40_n$ and imaging sequence commencement; and subtracting the time for the inverted $T_1$ magnetization of blood to recover to a selected magnitude near the zero crossing 56. This timing calculation is adjusted to account for a repeat time that permits less than full recovery of the longitudinal magnetization or for the use of an inversion pulse that tips the longitudinal magnetization less than 180°.

Alternately, the imaging sequence may be timed to occur a selected duration after preinversion pulse 42 such that it is in a preselected relationship with a zero crossing 56.

In another embodiment, the preinversion pulse 42 is applied only to selected portions or slices of the patient, specifically portions outside of the imaging slices or region. Preferably the conditioning pulse is applied as a slice selected inversion pulse or as a non-selective inversion pulse followed by a selective inversion pulse to reinvert the spins in the region of interest. In this case, the blood signal in the imaging region is not inverted by the inversion pulse. The timing is gauged to allow for flowing and mixing of the spin inverted blood into the region of interest. The inversion pulse may be less than 180° to reduce the time between the inversion pulse and the zero crossing.

Alternately, a presaturation technique may be utilized. The preinversion pulse 42 is replaced with saturation RF and gradient pulses which selectively dephase the longitudinal magnetization of both the blood and the heart tissue in regions adjacent the imaging region. The blood recovers analogous to curve 54 of FIG. 2B, however, it starts at about zero amplitude. The imaging window 44 is timed to occur when sufficient saturated blood has flowed into the imaging region that the net blood magnetization in the image region is substantially reduced.

Figure 1B:
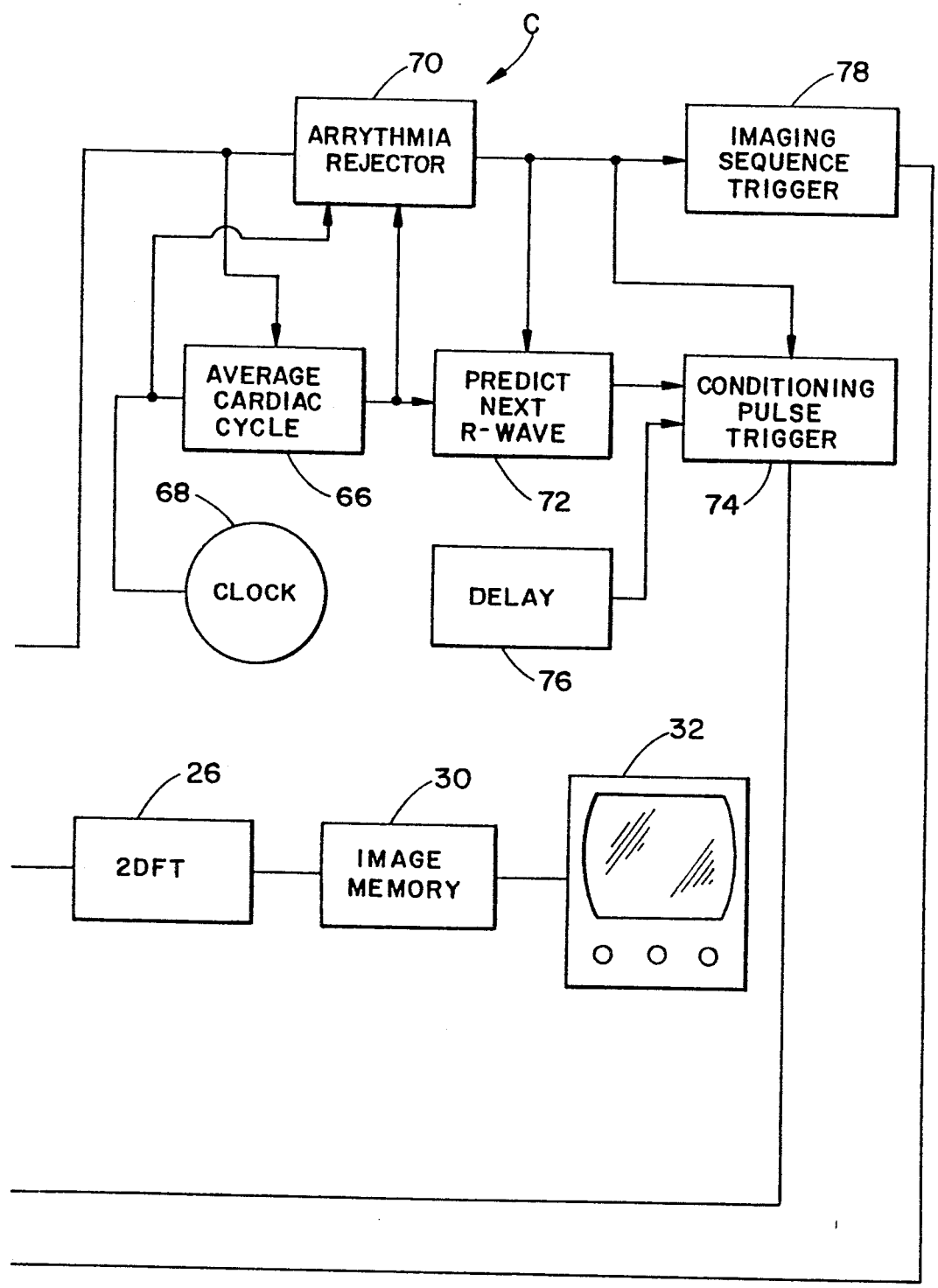

With reference again to FIG. 1, a cardiac monitoring means 60 includes a pick up unit 62 attached to the patient to monitor the cardiac cycle and an electronic signal processor 64 to ascertain a selected point in the cardiac cycle, e.g. the occurrence of the R-wave. The cardiac monitor electronics produces an output signal at each occurrence of the selected point in the cardiac cycle. An average cycle duration determining means 66 measures the amount of time between a selected point in the cardiac cycle with a clock 68. The average cycle time means produces an output signal which is a cumulative average of a selected number of cardiac cycles.

An arrythmia rejection means 70 compares the time of each cardiac cycle with the average. If the currently monitored cardiac cycle deviates more than a preselected tolerance from the average cycle time, it is rejected and not used for imaging or to compute the average cycle time. A prediction means 72 is triggered by the R-wave occurrence signal to predict the time at which the next R-wave will occur based on the average cardiac cycle time. A conditioning pulse enabling means 74 generates a signal which triggers the conditioning pulse generating means 34 to generate the preconditioning pulse 42. A selected delay means 76 provides an indication of an operator selected delay, TI, between the conditioning pulse 42 and the next imaging window 44. The conditioning pulse trigger means 74 subtracts the delay TI from the next predicted R-wave and triggers the preconditioning pulse at that time. An imaging sequence triggering means 78 is triggered by the occurrence of the R-wave to cause the imaging sequence control means 22 to start an imaging sequence. In this manner, the preconditioning pulse 42 is caused to occur a preselected duration before the next R-wave, which next R-wave triggers an imaging sequence, unless the arrythmia rejection means stops the sequence.

In addition to the imaging sequence illustrated in U.S. Pat. No. 4,728,890, various other imaging sequences may be utilized. The exact imaging sequence selected is determined by the nature of the information to be derived. Various spin echo, field echo, $T_1$ or $T_2$ weighted, with or without motion artifact suppression, single or multiple slice, and single or multiple echo image sequences may be selected. A conventional spin echo read out sequence may be utilized to produce a dark blood image with greatly reduced blood artifact.

Field echo sequences are preferred for cine acquisition. Such sequences combined with a pre-inversion pulse exhibit reduced blood signal and are preferred for dark blood cine studies, particularly when combined with presaturation schemes. In such an implementation, the inversion pulse is applied as described above, at a time in the previous cycle calculated such that the blood signal is at or near its zero crossing at the next R-wave. The cine field-echo sequence is started at a time when the blood signal is minimal and keeps the blood signal minimal by repeated application of additional saturation pulses outside the imaging region.

$T_1$ weighted spin echo sequences are the most common for cardiac imaging. $T_2$ weighted images can offer additional information about pathology. Preinversion is useful for reducing the blood signal in $T_2$ weighted imaging, particularly if a motion artifact suppression technique is used to reduce other motion and flow artifacts.

The motion artifact suppression technique of U.S. Pat. No. 4,728,890 reduces artifacts due both to flow and to gross motion of the heart and chest wall and the like. The sequence produces bright blood when flow rates are slow to moderate, when no presaturation or inversion is used. When the preinverted pulse is used, the image intensity is a function of the timing and relaxation parameters. Depending on the selected delay TI, the blood may be dark and the myocardium bright.

Single and multiple slice read out sequences may also be used. Because the blood signal intensity in the image is a function of flow effects as well as blood longitudinal magnetization, a dramatic reduction in artifacts due to

United States Patent Office

PTO – BOYERS, PA Duty Station

BEST AVAILABLE COPY

MISSING PAGE TEMPORARY NOTICE

PATENT # 5000182  FOR ISSUE DATE 3-19-1991

HAS BEEN SCANNED, BUT WITH MISSING PAGE(S). UPON RECEIVING OF MISSING PAGE(S), THE ENTIRE DOCUMENT WILL RE RESCANNED. PLEASE CALL IMAGE DATA ADMINISTRATION STAFF OF 557-6154 IF YOU HAVE A QUESTION. ASK FOR DAVE GROOMS, ANITA YOUNG OR POLA JONES.

THIS NOTICE IS FOR THE MISSING PAGE CONTAINING:

COLUMN # 7-8

N/A at Boyers
7/30/92

Data Conversion Operation
Boyers, Pa an imaging sequence means for applying an imaging sequence of radio frequency and gradient magnetic field pulses in the image region to generate magnetic resonance image data;

a preconditioning pulse means for applying a preconditioning radio frequency pulse in the image region, the radio frequency preconditioning pulse affecting a subsequent imaging sequence;

a cardiac monitor means for monitoring cardiac cycles of the patient;

a projecting means for projecting an occurrence of a preselected identifiable point in a next cardiac cycle, the projecting means being connected with the cardiac monitor means;

a first enabling means for enabling the preconditioning pulse means to apply the preconditioning pulse a preselected duration before the occurrence of the projected preselected identifiable point in the next cardiac cycle, the first enabling means being connected with the projecting means and the preconditioning pulse means;

a second enabling means for enabling the imaging sequence for applying the imaging sequence in coordination with the preselected identifiable point of the next cardiac cycle, the second enabling means being connected to the cardiac monitoring means and the imaging sequence means such that each imaging sequence is affected by the preconditioning pulse applied during a preceding cardiac cycle.

15. The apparatus as set forth in claim 14 wherein the cardiac monitor means monitors the cardiac cycles for at least the occurrence of an R-wave and wherein the projecting means projects the occurrence of the R-wave of the next cardiac cycle and the second enabling means enables the imaging sequence means in response to the monitored R-wave.

* * * * *